United States Patent [19]

Veber et al.

[11] Patent Number: 4,479,941
[45] Date of Patent: Oct. 30, 1984

[54] RENIN INHIBITORY PEPTIDES HAVING PHE[13] DELECTION

[75] Inventors: Daniel F. Veber, Ambler; Joshua S. Boger, Bryn Mawr; Mark G. Bock, Hatfield, all of Pa.

[73] Assignee: Merck & Co., Inc., Rahway, N.J.

[21] Appl. No.: 438,841

[22] Filed: Nov. 4, 1982

Related U.S. Application Data

[63] Continuation-in-part of Ser. No. 329,166, Dec. 10, 1981, abandoned.

[51] Int. Cl.[3] .................... C07C 103/52; A61K 37/02
[52] U.S. Cl. ............... 424/177; 260/112.5 R
[58] Field of Search ................. 260/112.5 R; 424/177

[56] References Cited

U.S. PATENT DOCUMENTS

| | | | |
|---|---|---|---|
| 3,784,686 | 1/1974 | Miller | 424/94 |
| 3,873,681 | 3/1975 | Müller | 424/94 |
| 4,185,096 | 1/1980 | Castro et al. | 424/177 |
| 4,269,827 | 5/1981 | Burton et al. | 424/177 |
| 4,384,994 | 5/1983 | Veber et al. | 260/112.5 R |

FOREIGN PATENT DOCUMENTS 7667001 6/1976 Japan.

OTHER PUBLICATIONS

Umezawa et al., J. Antibiot, (Tokyo), 23: 259–262, 1970.
Gross, et al., Science 175: 656, 1971.
Tewksbury, et al., Circulation 59, 60, Supp. II: 132 Oct. 1979.
Poulsen et al., Biochem. Biophys. Acta, 452:533–537, 1976.
Skeggs, Jr., et al., J. Exp. Med., 106:439–453, 1957.
Kokubu et al., Biochem. Pharmacol., 22: 3217–3223, 1973.
Burton et al., Biochemistry, 14: 3892–3898, 1975.
Poulsen et al., Biochemistry, 12: 3877–3882, 1973.
Haber and Burton, Fed. Proc. Fed. Am. Soc. Exp. Biol., 38: 2768–2773, 1979.
Marshall, Federation Proc., 35: 2494–2501, 1976.
Burton et al., Proc. Natl. Acad. Sci., U.S.A., 77: 5476–5479, 9/198.
Suketa et al., Biochemistry, 14: 3188, 1975.
Swales, Pharmac. Ther., 7: 173–201, 1979.
Kokubu et al., Nature, 217: 456–457, Feb. 3, 1968.
Matsushita et al., J. Antibiotics, 28: 1016–1018, Dec. 1975.
Lazar et al., Biochem. Pharma., 23: 2776–2778, 1974.
Miller et al., Biochem. Pharma., 21: 2941–2944, 1972.
Haber, Clinical Science, 59: 7s–19s, 1980.
Rich et al., J. Org. Chem., 43: 3624, 1978.
J. Med. Chem., 23: 27, 1980.
Chemical Abstracts, 86, 147, (1977), Abst. No. 86: 27724p.
Powers et al., *Acid Proteases, Structure, Function, and Biology*, Plenum Press, 141–157, (1977).
Tang, J., *Trends in Biochemical Sci.*, 1, 205–208, (1976).

*Primary Examiner*—Delbert R. Phillips
*Assistant Examiner*—F. T. Moezie
*Attorney, Agent, or Firm*—Raymond M. Speer; Daniel T. Szura

[57] ABSTRACT

Renin inhibitory peptides of the formula

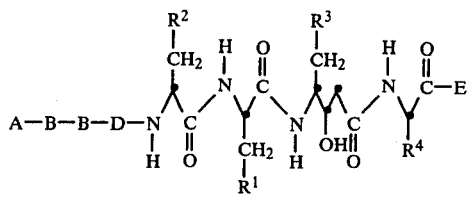

and analogs thereof inhibit renin and are useful for treating various forms of renin-associated hypertension and hyperalaosteronism.

8 Claims, No Drawings

RENIN INHIBITORY PEPTIDES HAVING PHE[13] DELECTION

REFERENCE TO RELATED APPLICATIONS

This application is a continuation-in-part of application Ser. No. 329,166, filed Dec. 10, 1981, now abandoned.

BACKGROUND OF THE INVENTION

1. Field of the Invention

The present invention is concerned with novel peptides which inhibit renin.

The present invention is also concerned with pharmaceutical compositions containing the novel peptides of the present invention as active ingredients, with methods of treating renin-associated hypertension and hyperaldosteronism, with diagnostic methods which utilize the novel peptides of the present invention, and with methods of preparing the novel peptides of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate the renin-angiotensin system have met with success in the use of inhibitors of angiotensin I converting enzyme. In view of this success, it seems reasonable to conclude that a specific inhibitor of the limiting enzymatic step that ultimately regulates angiotensin II production, the action of renin on its substrate, would be at least equally successful. Thus, an effective inhibitor of renin has been long sought as both a therapeutic agent and as an investigative tool.

2. Brief Description of the Prior Art

There has been substantial interest in the synthesis of useful renin inhibitors for many decades; and the following table lists the major classes of renin inhibitors that have been studied, as well as their inhibition constants ($K_i$):

| Class | $K_i$ (M) |
|---|---|
| Renin antibody | probably $10^{-6}$ |
| Pepstatin | $10^{-6}$–$10^{-7}$ |
| Phospholipids | $10^{-3}$ |
| Substrate analogs | |
| Tetrapeptides | $10^{-3}$ |
| Octa- to tridecapeptides | $10^{-5}$–$10^{-6}$ |

Umezawa et al., in *J. Antibiot.* (Tokyo) 23: 259–262, 1970, reported the isolation of a peptide from actinomyces that was an inhibitor of aspartyl proteases such as pepsin, cathepsin D, and renin. This peptide, known as pepstatin, was found by Gross et al., *Science* 175: 656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. The structure of pepstatin is shown below:

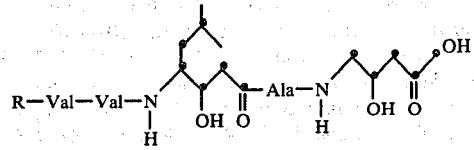

To date, many efforts have been made to prepare a specific renin inhibitor based on substrate analogy. Since the human renin substrate has only recently been elucidated (Tewksbury et al., *Circulation* 59, 60, Supp. II: 132, Oct. 1979), heretofore substrate analogy has been based on the known pig renin substrate. While the human and pig renin substrates are not the same, the substrate analogy based on pig renin has always been considered acceptable in the art as predictive of human renin inhibitory activity because of the closely related activity of the two renins. Thus, while pig renin does not cleave the human renin substrate, human renin, on the other hand, does cleave the pig renin substrate. See Poulsen et al., *Biochim. Biophys. Acta* 452: 533–537, 1976; and Skeggs, Jr. et al., *J. Exp. Med.* 106: 439–453, 1957. Moreover, the human renin inhibitory activity of the peptides of the present invention most active in inhibiting pig renin has been confirmed, thus providing further evidence of this accepted correlation between human and pig renin activity.

It has been found, for example, using pig renin substrate analogy, that the octapeptide sequence extending from histidine-6 through tyrosine-13 has kinetic parameters essentially the same as those of the full tetradecapeptide renin substrate. The amino acid sequence of the octapeptide in pig renin substrate is as follows:

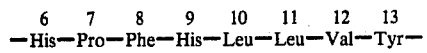

Renin cleaves this substrate between Leu[10] and Leu[11].

Kokubu et al., *Biochem. Pharmacol.* 22: 3217–3223, 1973, synthesized a number of analogs of the tetrapeptide found between residues 10 to 13, but while inhibition could be shown, inhibitory constants were only of the order of $10^{-3}$M.

Analogs of a larger segment of renin substrate were also synthesized: Burton et al., *Biochemistry* 14: 3892–3898, 1975, and Poulsen et al., *Biochemistry* 12: 3877–3882, 1973. Two of the major obstacles which had to be overcome to obtain an effective renin inhibitor useful in vivo were lack of solubility and weak binding (large inhibitory constant). Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success. Various modifications designed to increase binding to renin have also been made, but here too, with only limited success. For a more detailed description of past efforts to prepare an effective inhibitor of renin, see Haber and Burton, *Fed. Proc. Fed. Am. Soc. Exp. Biol.* 38: 2768–2773, 1979.

For other articles describing previous efforts to devise renin inhibitors, see Marshall, *Federation Proc.* 35: 2494–2501, 1976; Burton et al., *Proc. Natl. Acad. Sci. USA* 77: 5476–5479, Sept. 1980; Suketa et al., *Biohemis-*

*try* 14: 3188, 1975; Swales, *Pharmac. Ther.* 7: 173-201, 1979; Kokubu et al., *Nature* 217: 456-457, Feb. 3, 1968; Matsushita et al., *J. Antibiotics* 28: 1016-1018, Dec. 1975; Lazar et al., *Biochem. Pharma:* 23: 2776-2778, 1974; Miller et al., *Biohem. Pharma.* 21: 2941-2944, 1972; Haber, *Clinical Science* 59:7s-19s, 1980; and Rich et al., *J. Org. Chem.* 43: 3624, 1978, and *J. Med. Chem.* 23: 27, 1980.

DETAILED DESCRIPTION OF THE INVENTION AND PREFERRED EMBODIMENTS

In accordance with the present invention there are provided renin inhibitory peptides of the formula:

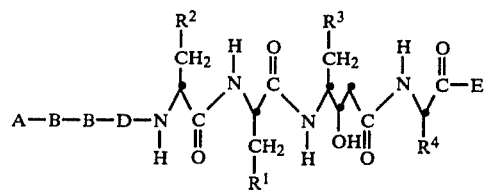   (I.)

wherein:
A is hydrogen;

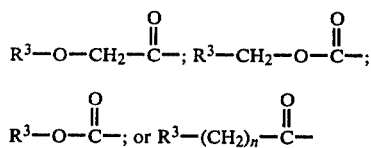

where n is 0 to 5 and $R^3$ has the same meaning as set out further below, and may additionally be hydrogen;

B is absent; glycyl; sarcosyl; or

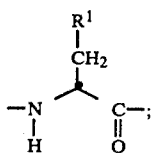

D is absent; or

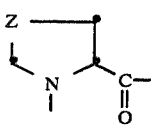

where Z is $(CH_2)_n$ and n is 1 or 2; or —S—;

$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

$R^3$ is $C_{3-6}$ alkyl; $C_{3-7}$ cycloalkyl; phenyl; or $C_{3-7}$cycloalkyl or phenyl mono-substituted with a member selected from the group consisting of methyl, trifluoromethyl, hydroxy, methoxy, fluoro, chloro, bromo, and iodo;

$R^4$ is hydrogen; or

where $R^5$ is hydrogen; $C_{1-4}$ alkyl; hydroxy; or $C_{3-7}$ cycloalkyl; and

E is

   (1)

where
Y is —NH— or —O—;
n is 0 to 5; and
$R^6$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di- $C_{1-4}$ alkylamino, and halo; amino; mono-, di-, or tri- $C_{1-4}$alkylamino; guanidyl; heterocyclic; or heterocyclic substituted with up to five members independently selected from the group consisting of $C_{1-6}$alkyl, hydroxy, trifluoromethyl; $C_{1-4}$alkoxy, halo, aryl, aryl $C_{1-4}$alkyl, amino, and mono- or di-$C_{1-4}$alkylamino;

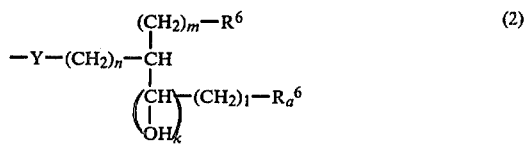   (2)

where
Y is as defined above;
n is 0 or 1;
k is 0 or 1;
l is 1 to 4;
m is 1 to 4; and
$R^6$ and $R_a^6$ may be the same or different and have the same meaning as $R^6$ above and $R_a^6$ may additionally be

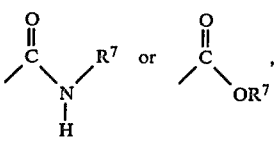

where $R^7$ is hydrogen or $C_{1-3}$alkyl; or

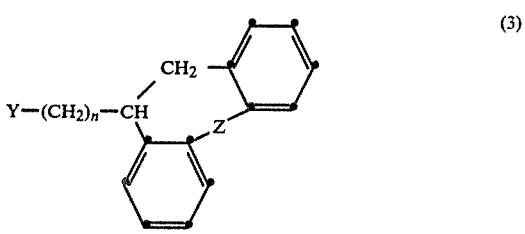   (3)

where
Y is as defined above;

n is 0 or 1; and
Z is (a) 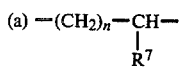

where
n is 0 or 1; and
$R^7$ is as defined above; or (b) 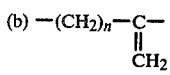

where
n is 0 or 1;
wherein all of the asymmetric carbon atoms have an S configuration, except for those in the B, D, and E substituents, which may have an S or R coniguration; and a pharmaceutically acceptable salt thereof.

While both the S and R chiralities for asymmetric carbon atoms in the E substituent are included in the peptides of the present invention, preferred chiralities are indicated in the description which follows.

In the above definitions, the term "alkyl" is intended to include both branched and straight chain hydrocarbon groups having the indicated number of carbon atoms.

The aryl substituent represents phenyl, naphthyl, or biphenyl.

The heterocyclic substituent recited above represents any 5- or 6-membered aromatic ring containing from one to three heteroatoms selected from the group consisting of nitrogen, oxygen, and sulfur; having various degrees of saturation; and including any bicyclic group in which any of the above heterocyclic rings is fused to a benzene ring. Heterocyclic substituents in which nitrogen is the heteroatom are preferred, and of these, those containing a single nitrogen atom are preferred. Fully saturated heterocyclic substituents are also preferred. Thus, piperidine is a preferred heterocyclic substituent. Other preferred heterocyclic substituents are: pyrryl, pyrrolinyl, pyrroidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Where the heterocyclic substituent itself is substituted, it is preferred that the substituent be aryl$C_{1-4}$alkyl.

The novel renin inhibitory peptides of the present invention may also be described in terms of common amino acid components and closely related analogs thereof, in accordance with the following formula:

$$A-B-B-D-F-G-Sta-H-E \quad (II.)$$

The A,B,D, and E components correspond to the same portions of Formula I.

In Formula II, Sta represents the unusual amino acid statine and its closely related analogs, and its presence constitutes a unique feature of the renin inhibitory peptides of the present invention. Statine may be named as 4(S)-amino-3(S)-hydroxy-6-methylheptanoic acid, and may be represented by the following formula:

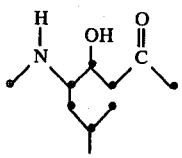 (III)

As shown in Formula III above, the delta-substituent in naturally-occurring statine is isopropyl, or a leucine sidechain, essentially. As shown in Formula I by the $R^3$ substituents, the isopropyl group may be replaced by higher alkyl groups up to six carbon atoms, cycloalkyl groups containing from three to seven carbon atoms, phenyl, and phenyl mono-substituted with a member selected from the group consisting of methyl, trifluoromethyl, hydroxy, methoxy, fluoro, chloro, bromo, and iodo. The phenyl substituent is especially preferred. These modifications of the naturally-occurring statine structure are in accordance with the hydrophobicity considered necessary to maintain the inhibitory activity of the total peptide.

The remaining common amino acid components of Formula II are as follows:
A has the same meaning as above in Formula I;
B is absent, Gly, Ala, Val, Leu, Ile, Phe, Tyr, Trp, His, Lys, Orn, Arg, or Met;
D is absent or Pro;
F is Ala, Leu, Phe, Tyr, or Trp;
G is Ala, Leu, Phe, Tyr, Trp, His, Lys, Orn, Arg, or Met;
H is the same as F and may additionally be Ser, Gly, Val, Ile, or Thr; and
E has the same meaning as above in Formula I.

It will be understood that closely related analogs of the above common amino acids, for example, aliphatic amino acids in addition to Ala, Val, Leu, and Ile, such as α-aminobutyric acid (Abu), and substituted phenyl derivatives of Phe, are included in the broad description of the novel inhibitory peptides of the present invention represented by Formula I and its definitions. Thus, the peptides of Formula II and its definitions, including the derivatives of naturally-occurring statine represented by the definitions of the $R^3$ substituent in Formula I, represent preferred peptides of the present invention.

Especially preferred inhibitory peptides of the present invention are the following:

IBU[1]—His-Pro-Phe-His-Sta-Leu-benzylamide;
IBU—His-Pro-Phe-His-Sta-Leu-2-phenylethylamide;
IBU—His-Pro-Phe-His-Sta-Leu-3-phenylpropylamide;
IBU—His-Pro-Phe-His-Sta-Leu-1,2-diphenylethylamide;
BOC[2]—Phe-His-Sta-Leu-(+)[3]-1,2-diphenylethylamide;
BOC—Phe-His-Sta-Leu-(−)-1,2-diphenylethylamide;
BOC—Phe-His-Sta-Leu-benzylamide;
BOC—Phe-His-Sta-Leu-(+)-α-phenylethylamide;
BOC—Phe-His-Sta-Leu-(−)-α-phenylethylamide;
BOC—Phe-His-Sta-Leu-(+)-α-naphthylethylamide;
BOC—Phe-His-Sta-Leu-(−)-α-naphthylethylamide;
BOC—Phe-His-Sta-Leu-p-chlorobenzylamide;

BOC—Phe-His-Sta-Leu-p-methoxyenzylamide;
BOC—Phe-His-Sta-Leu-10,11-dihydro-5H-dibenzo[a,d]-cycloheptenamide;
BOC—Phe-His-Sta-Leu-D,L-threo-1,2-diphenyl-2-hydroxyethylamide;
BOC—Phe-His-Sta-Leu-Sta;
BOC—Phe-His-AHPPA[4]-Lleu-benzylamide;
Acetyl—Phe-His-AHPPA-Leu-benzylamide;
BOC—Phe-His-Sta-Leu-(2-amidomethylpyridine);
BOC—Phe-His-Sta-Leu-(4-amidomethylpyridine);
BOC—Phe-His-Sta-Leu-(4-amido-1-benzylpiperidine);
BOC—Phe-His-Sta-Leu-[N-(3-amidopropyl)diethanolamine];
BOC—Phe-His-AHPPA-Leu-(2-amidomethylpyridine);
BOC—Phe-His-ACHPA[5]-Ile-(2-amidomethylpyridine);
IVA[6]-His-D-Pro-Phe-His-ACHPA-Ile-(2-amidomethylpyridine).

[1]IBU=Iso-butyryl.
[2]BOC=Tert-butyloxycarbonyl.
[3](+) refers to the optical rotation of the amine.
[4]AHPPA=(3S, 4S)-4-amino-3-hydroxy-5-phenylpentanoic acid.
[5]ACHPA=(3S, 4S)-4-amino-5-cyclohexyl-3-hydroxypentanoic acid.
[6]IVA=Iso-valeryl.

The inhibitory peptides of the present invention may be better appreciated in terms of substrate analogy from the following illustration of Formula I alongside the octapeptide sequence of a portion of the pig renin substrate, which renin cleaves between Leu[10] and Leu[11]:

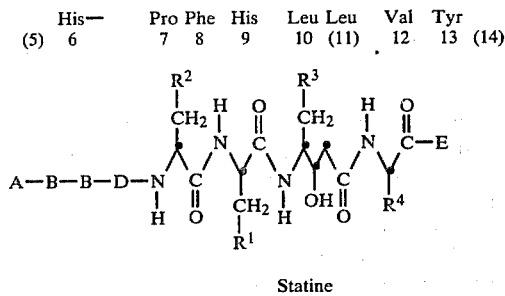

Statine

As can be seen, a unique aspect and essential feature of the present invention is the substitution of the single statine amino acid component for the double amino acid sequence: Leu[10]-Leu[11] in the endogenous pig renin substrate. It is believed that substitution of statine for both leucine amino acids rather than just one leucine results in an improved substrate analogy due to the greater linear extent of statine as compared to a single leucine component. Thus, statine more closely approximates Leu-Leu in linear extent, and thereby provides a better "fit" to the renin enzyme.

The inhibitory peptides of the present invention may also be better appreciated in terms of substrate analogy from the following illustration of Formula I alongside the octapeptide sequence of a portion of the human renin substrate, which renin cleaves between Leu[10] and Val[11]:

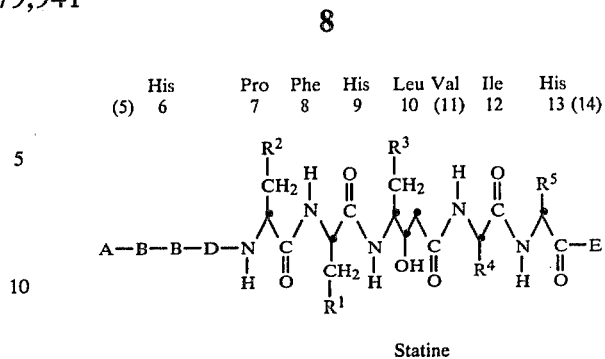

Statine

As can be seen, a unique aspect and essential feature of the present invention is the substitution of the single statine amino acid component for the double amino acid sequence: Leu[10]-Val[11] in the endogenous human renin substrate. It is believed that substitution of statine for both the leucine and valine amino acids rather than just the leucine results in an improved substrate analogy due to the greater linear extent of statine as compared to a single leucine component. Thus, statine more closely approximates Leu-Val in linear extent, and thereby provides a better "fit" to the human renin enzyme.

In the endogenous substrate it is also preferred to substitute Leu for Val[12] and Phe for Tyr[13] in order to enhance the inhibitory activity of the resulting peptide.

The Formula I compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, nemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persultate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel peptides of the present invention possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a peptide of the formula:

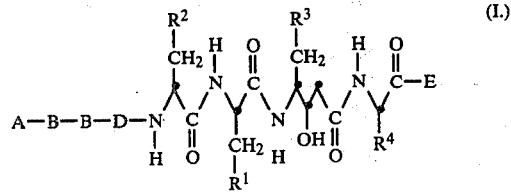

wherein A, B, D, $R^1$, $R^2$, $R^3$, $R^4$, and E have the same meaning as recited further above for Formula I; wherein all of the asymmetric carbon atoms have an S configuration, except for those in the B, D, and E substituents, which may have an S or R configuration, and a pharmaceutically acceptable salt thereof.

Also, in accordance with the present invention there is still further provided a method or treating renin-associated hypertension and hyperaldosteronism, comprising administering to a patient in need of such treatment, a therapeutically effective amount of a peptide of the formula:

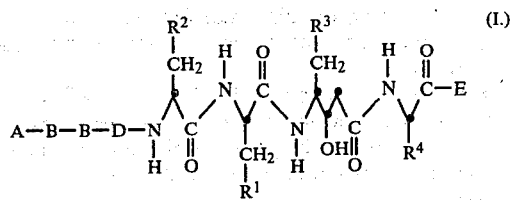

wherein A, B, D, $R^1$, $R^2$, $R^3$, $R^4$, and E have the same meaning as recited further above for Formula I; wherein all of the asymmetric carbon atoms have an S configuration, except for those in the B, D, and E substituents, which may have an S or R configuration; and a pharmaceutically acceptable salt thereof.

The renin inhibitory novel peptides of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 0.1 to 10 mg per kg of body weight.

Both in vivo and in vitro methods may be employed. In the in vivo method, a novel peptide or the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel peptide of the present invention and, after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptides of the present invention may be prepared in accordance with well-known procedures for preparing peptides from their constituent amino acids, which will be described in more detail below. The unusual amino acid, statine, may be prepared in accordance with the procedure described by Rich et. al., *J. Org. Chem.* 43: 3624 (1978).

A general method of preparation may be described in the following terms:

A method of preparing a peptide of formula I, said peptide being comprised of from five to seven amino acids identified as I through VII, amino acid (AA) I being at the C-terminus of said peptide, to which substituent E is attached, and amino acid (AA) VII being at the N-terminus of said peptide, to which substituents A-B-B-D are attached, comprising the steps of:

(A) treating the desired ester or amide of the C-terminus amino acid (AA I) with the next adjacent amino acid (AA II) of said peptide, the amino group of said amino acid being protected by a protecting group, in the presence of a condensing agent, whereby a dipeptide of the two amino acids (AA I and II) is formed;

(B) deprotecting the dipeptide formed in Step (A) by removing the protecting group from the amino group of AA II;

(C) treating the dipeptide of AA I and AA II with AA III, the amino group of which is protected by a protecting group, in the presence of a condensing agent, whereby a tripeptide of AA I, AA II and AA III is formed;

(D) deprotecting the tripeptide formed in Step (C) by removing the protecting group from the amino group of AA III;

(E) forming a quadripeptide up to a heptapeptide of AA I, through AA IV, AA V, AA VI or AA VII, by repeating the procedure of Step (C) using protected AA IV through protected AA VII;

(F) deprotecting the quadripeptide through heptapeptide formed in Step (E) to give the peptide of formula I wherein A is hydrogen; and optionally (G) treating the quadripeptide through heptapeptide formed in Step (F) with

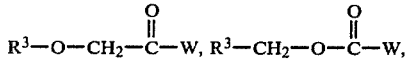

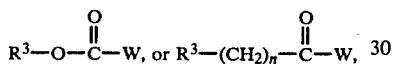

where $R^3$ and n are as defined above and W is an acid halide, anhydride, or other carboxyl activating group, to give the peptide of formula I wherein A is other than hydrogen and optionally (H) treating the quadripeptide through heptapeptide formed in Steps (F) or (G) where an ester of AA I is employed with hydrazine to give the corresponding hydrazide, followed by treatment of said hydrazide with acidic nitrite to give the corresponding acyl azide, followed by treatment of said acyl azide with the appropriate amine compound to give the desired E substituent in the peptide of Formula I;

said method also comprising, where necessary, protection of sidechain substituents of the component amino acids AA I through AA VII, with deprotection being carried out as a final step; said method also comprising any combination of the steps set out above, whereby the amino acids I through VII and substituents A, B, C, and E are assembled in any desired order to prepare the peptide of formula I; and said method also comprising employment of the steps set out above in a solid phase sequential synthesis, whereby in the initial step the carboxyl group of the selected amino acid is bound to a synthetic resin substrate while the amino group of said amino acid is protected, followed by removal of the protecting group, the succeeding steps being as set out above, the peptide as it is assembled being attached to said synthetic resin substrate; followed by a step of removing the peptide of Formula I from said synthetic resin substrate: (a) by strong acid cleavage to give E=OH; (b) by transesterification with a $C_{1-4}$ alkanol to give E=O-$C_{1-4}$alkyl (followed by hydrolysis to give E=OH); or (c) by ammonolysis with NH$_2$R' where R' is hydrogen or $C_{1-4}$alkyl; and after removal of the peptide of Formula I from said synthetic resin substrate by transesterification to form the ester thereof as recited above, optionally the step of teating said ester thereof in accordance with the procedures described in Step (H) above to give the desired E substituent in the peptide of Formula I; removal of sidechain protecting groups being accomplished either before or after removal of the peptide of Formula I from said synthetic resin substrate.

Preparation of the peptides of Formula I having the desired E substituent, as described above in Step (H), may be illustrated as follows for the particular case where E=benzylamide (and PEP represents the remaining portion of the peptide of Formula I):

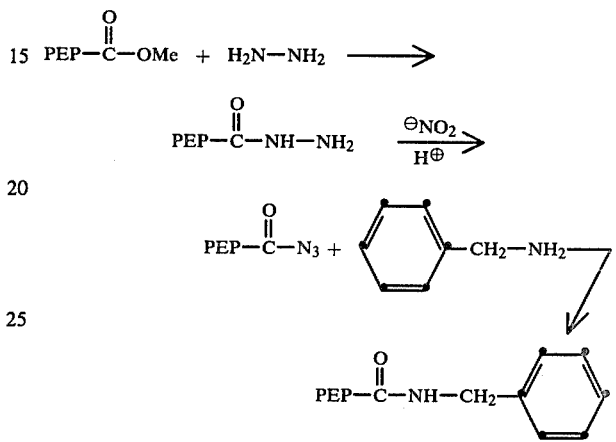

The phenyl analog of statine, (3S,4S)-4-amino-3-hydroxy-5-phenylpentanoic acid (AHPPA) can be prepared in accordance with the procedure described by Rich et al., *J. Med. Chem.* 23: 27–33 (1980).

The cyclohexylalanine analog of statine, (3S,4S)-4-amino-5-cyclohexyl-3-hydroxypentanoic acid (ACHPA) can be prepared by catalytic hydrogenation (using H$_2$/Rh on alumina, or other suitable catalyst) of the BOC-AHPPA, prepared as described in the paragraph immediately above. Alternatively, this and similar statine analogs can be prepared in accordance with the procedure described for statine, where the BOC-Leu starting material is replaced with the amino acid containing the desired side chain. Thus, BOC-ACHPA can also be prepared starting from BOC-L-cyclohexylalanine, itself prepared, for example, by catalytic reduction of BOC-Phe, in the same manner as described for BOC-AHPPA.

The novel inhibitory peptides of the present invention are prepared by using the solid phase sequential synthesis technique.

In the following description several abbreviated designations are used for the amino acid components, certain preferred protecting groups, reagents and solvents. The meanings of such abbreviated designations are given below in Table I.

TABLE I

| Abbreviated Designation | Amino Acid |
|---|---|
| AHPPA | (3S,4S)—4-amino-3-hydroxy-5-phenylpentanoic acid |
| ACHPA | (3S,4S)—4-amino-5-cyclohexyl-3-hydroxypentanoic acid |
| Ala | L-alanine |
| Arg | L-arginine |
| Gly | L-glycine |
| His | D or L-histidine |
| Ile | L-isoleucine |

TABLE I-continued

| Abbreviated Designation | Amino Acid |
|---|---|
| Leu | L-leucine |
| Lys | L-lysine |
| Met | L-methionine |
| Orn | L-ornithine |
| Phe | L-phenylalanine |
| Pro | D or L-proline |
| Ser | L-serine |
| Sar | L-sarcosine (N—methylglycine) |
| Sta | (3S,4S)—statine |
| Thr | L-threonine |
| Trp | L-tryptophan |
| Tyr | L-tyrosine |
| Val | L-valine |
| Protecting Groups | |
| BOC | tert-butyloxycarbonyl |
| CBZ | benzyloxycarbonyl |
| DNP | dinitrophenyl |
| OMe | methyl ester |
| Activating Groups | |
| HBT | 1-hydroxybenzotriazole |
| Condensing Agents | |
| DCCI | dicyclohexylcarbodiimide |
| DPPA | diphenylphosphorylazide |
| Reagents | |
| TEA | triethylamine |
| TFA | trifluoroacetic acid |
| Solvents | |
| A | ammonium hydroxide (conc.) |
| AcOH | acetic acid |
| C | chloroform |
| DMF | dimethylformamide |
| E | ethyl acetate |
| M | methanol |
| P | pyridine |
| THF | tetrahydrofuran |
| W | water |

The synthesis of the peptides of the present invention by the solid phase technique is conducted in a stepwise manner on chloromethylated resin. The resin is composed of fine beads (20–70 microns in diameter) of a synthetic resin prepared by copolymerization of styrene with 1–2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as ONP ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyoxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoroacetic acid, or hydrogen chloride in ethyl acetate).

The OH group of Thr and Ser can be protected by the Bzl group and the -amino group of Lys can be protected by the INOC group or the 2-chlorobenzyloxycarbonyl (2-Cl-CBZ) group. Neither group is affected by TFA, used for removing BOC protecting groups. After the peptide is formed, the protective groups, such as 2-Cl-CBZ and Bzl, can be removed by treatment with HF or by catalytic hydrogenation.

After the peptide has been formed on the solid phase resin, it may be removed from the resin by a variety of methods which are well known in the art. For example the peptide may be cleaved from the resin with hydrazine, by ammonia in methanol, or by methanol plus a suitable base.

Preparation of the novel inhibitory peptides of the present invention utilizing the solid phase technique is illustrated in the following examples. These examples have actually been carried out. However, they are not intended to be any limitation of the present invention.

EXAMPLE 1

N-Isobutyryl-L-histidyl-L-prolyl-L-phenylalanyl-L-histidyl-(3S,4S)-statyl-L-leucyl-benzylamide The title peptide was prepared by standard solid phase methodology, as described in Erickson and Merrifield, Proteins, 3rd et., 2:257–527, 1976, using a Beckman Model 990B peptide synthesizer to carry out the operations according to the attached programs.

A.

Isobutyryl-L-histidyl-L-prolyl-L-phenylalanyl-L-histidyl-(3S,4S)-statyl-L-leucyl-O-Resin The starting polymer was BOC-Leu esterified to 2% cross-linked polystyrene-divinylbenzene (6 mmol, 5.00 g). The $N^\alpha$-BOC derivatives of Sta, His-DNP, Phe, and Pro were coupled using dicyclohexylcarbodiimide with an equivalent of the additive 1-hydroxybenzotriazole hydrate. The Sta was prepared in accordance with Rich et al., J. Org. Chem. 43:3624, 1978. The BOC-group was removed with 40% trifluoroacetic acid. A coupling of 60 minutes followed by a recoupling of 120 minutes (2.5 equivalents each time of BOC-amino acid) were used for each amino acid, except for Sta. These coupling times had been previously demonstrated to give complete coupling (as judged by the method of Kaiser) in this sequence. In order to conserve the amounts of Sta employed, an initial coupling using 1.08 equivalents of $N^\alpha$-BOC-Sta (in 20 ml of 1:1 $CH_2Cl_2$/DMF) for 72 hrs gave approximately 95% complete reaction. The addition of an additional 0.12 equivalents of $N^\alpha$-BOC-Sta plus an equal amount of DCCI to the stirring suspension gave complete coupling after an additional 18 hrs. The N-terminal isobutyryl group was coupled for 60 minutes as the symmetrical anhydride generated in situ from 5.0 equivalents of isobutyric acid and 2.5 equivalents of DCCI. This was followed by a recoupling for 120 minutes using 2.5 equivalents of isobutyric acid, HBT, and DCCI. The DNP protecting groups on His were removed in the final program using two 25-minute treatments with 10% thiophenol in DMF. The finished resin-peptide (2.70 g) was dried and suspended in 40 ml of dry methanol.

| SCHEDULE OF STEPS FOR 6 MMOL RUN | | | |
|---|---|---|---|
| Step | Solvent/Reagent | Vol. (ml) | Mix time (min) |
| Coupling Program 1 | | | |
| 1 | $CH_2Cl_2$ | 6 × 60 | 2 |
| 2 | 40% TFA in $CH_2Cl_2$ | 1 × 60 | 2 |
| 3 | 40% TFA in $CH_2Cl_2$ | 1 × 60 | 25 |
| 4 | $CH_2Cl_2$ | 3 × 60 | 2 |
| 5 | 10% TEA in $CH_2Cl_2$ | 2 × 60 | 5 |
| 6 | $CH_2Cl_2$ | 3 × 60 | 2 |
| 7 | BOC—amino acid, HBT in 1:1 DMF/$CH_2Cl_2$ | 40 | 5 |
| 8 | 1.0 M DCCI in $CH_2Cl_2$ | 15 | 60 |
| 9 | DMF | 1 × 60 | 2 |
| 10 | MeOH | 2 × 60 | 2 |
| 11 | $CH_2Cl_2$ | 1 × 60 | 2 |
| Re-Couple Program 2 | | | |
| 1 | $CH_2Cl_2$ | 1 × 60 | 2 |
| 2 | 10% TEA in $CH_2Cl_2$ | 2 × 60 | 5 |
| 3 | $CH_2Cl_2$ | 3 × 60 | 2 |
| 4 | BOC—amino acid, HBT in 1:1 DMF/$CH_2Cl_2$ | 40 | 5 |
| 5 | 1.0 M DCCI in $CH_2Cl_2$ | 15 | 120 |
| 6 | DMF | 1 × 60 | 2 |
| 7 | MeOH | 2 × 60 | 2 |
| 8 | $CH_2Cl_2$ | 5 × 60 | 2 |
| Program 3 (DNP removal) | | | |
| 1 | $CH_2Cl_2$ | 1 × 60 | 2 |
| 2 | DMF | 2 × 60 | 2 |
| 3 | 10% phenylthiol in DMF | 1 × 60 | 25 |
| 4 | DMF | 1 × 60 | 2 |
| 5 | 10% TEA in $CH_2Cl_2$ | 1 × 60 | 2 |
| 6 | DMF | 2 × 60 | 2 |
| 7 | 10% phenylthiol in DMF | 1 × 60 | 25 |
| 8 | DMF | 3 × 60 | 2 |
| 9 | MeOH | 2 × 60 | 2 |
| 10 | $CH_2Cl_2$ | 2 × 60 | 2 |
| 11 | MeOH | 2 × 60 | 2 |
| 12 | $CH_2Cl_2$ | 2 × 60 | 2 |
| 13 | MeOH | 2 × 60 | 2 |

B. Isobutyryl-L-histidyl-L-prolyl-L-phenylalanyl-L-histidyl-(3S,4S)-statyl-L-leucine methyl ester To the suspension prepared in Step A above was added 10 ml diisopropylethylamine, and the reaction mixture was stirred under a dry nitrogen atmosphere for 18 hours. The reaction mixture was then filtered and the yellow solution was evaporated under reduced pressure to give 1.4 g of crude methyl ester. This crude product was dissolved in 50 ml of methylene chloride and washed with water. The methylene chloride layer was dried over sodium sulfate and evaporated to give 1.1 g of yellow powder. This material was chromatographed on a silica column (160 g, 0.04–0.063 mmol) packed and eluted with chloroform/methanol/water/acetic acid-120:20:1.6:0.4. The pure methyl ester (thin layer chromatography on silica-chloroform/methanol/water-80:20:2, Rf=0.43) was obtained by evaporation of the appropriate fractions and precipitation from 3 ml of methylene chloride/50 ml of petroleum ether. Yield was 0.74 g.

C. Isobutyryl-L-histidyl-L-prolyl-L-phenylalanyl-L-histidyl-(3S,4S)-statyl-L-leucine hydrazide A portion of (0.44 g) of the ester prepared in Step B above was converted to the hydrazide by dissolving it in 2 ml of a 1:1 mixture of dry methanol and anhydrous hydrazine. After a few minutes the solution was evaporated to dryness, at 30° C., and the crude hydrazide was dissolved in 15 ml of n-butanol and washed 5 times with an equal volume of water containing a small amount of sodium chloride. The n-butanol layer was then evaporated and the hydrazide was precipitated from methylene chloride/petroleum ether. The yield was 0.41 g of a single material; thin layer chromatography (silica) 80:10:1-chloroform/methanol/conc. ammonia, Rf=0.12 (compare Rf=0.19 for the methyl ester). The material was over 99% pure as determined by high performance liquid chromatography.

D. N-Isobutyryl-L-histidyl-L-prolyl-L-phenylalanyl-L-histidyl-(3S,4S)-statyl-L-leucylbenzylamide The hydrazide prepared in Step C above can be converted by acidic nitrite to its corresponding acyl azide, and coupled to a wide variety of amines. Thus, 0.10 g of the hydrazide (0.10 mmol) was dissolved in 0.5 ml of dry, degassed dimethylformamide, and cooled to −30° C. under a nitrogen atmosphere. To this cold solution was added 1.1 mmol of fresh 7.1N hydrochloric acid in dry tetrahydrofuran. To this acidic solution was then added 15 μl of isoamylnitrite over a period of 10 minutes. After approximately 1 hour, there was added 1.1 mmol of diisopropylethylamine, and the pH was adjusted with additional base to 7 (using pH 6-8 paper). To this solution of the acyl azide was added 2 equivalents (0.2 mmol) of benzylamine, and the reaction mixture was held at −20° C. for 18 hours. The reaction solution was evaporated, and the resulting yellow oil was triturated with ether. The remaining solid was dissolved in 10 ml of n-butanol and washed twice with water, once with 5% sodium bicarbonate, and twice with sodium chloride solution. The butanol layer was then evaporated, dissolved in 10 ml methylene chloride, and the product was precipitated with 50 ml of ether. The yield was 60 mg showing a single spot of thin layer chromatography 80:20:2-chloroform/methanol/conc. ammonia, Rf=0.47. The product was 93.1% pure, as determined by high performance liquid chromatography, and had an acceptable amino acid analysis: His 1.98, Pro 0.96, Phe 1.03, and Leu 1.01. A 300 MHz 'HNMR spectrum was consistent with the desired structure.

EXAMPLE 2-26

Following the standard solid phase methodology described above in Example 1, additional inhibitory peptides of the present invention were prepared. The peptides prepared are set out in the following table, wherein the subscribed numerical value for each amino acid indicates the results of the Spinco amino acid analysis.

| Exm. No. | Peptide |
|---|---|
| 2 | |

| Exm. No. | Peptide |
|---|---|
| 2 | IBU—His—Pro—Phe—His—Sta—Leu—NH—(CH₂)₂—C₆H₅<br>      1.01 1.00 0.98 1.01     1.00<br>[-2-phenylethylamide] |
| 3 | IBU—His—Pro—Phe—His—Sta—Leu—NH—(CH₂)₃—C₆H₅<br>      0.99 1.00 1.01 0.99     1.01<br>[-3-phenylpropylamide] |
| 4 | IBU—His—Pro—Phe—His—Sta—Leu—NH—(CH₂)₄—C₆H₅<br>      1.02 0.97 1.01 1.02     0.99<br>[-4-phenylbutylamide] |
| 5 | IBU—His—Pro—Phe—His—Sta—Leu—NH—CH(C₆H₅)CH₂C₆H₅<br>      1.01 1.04 0.97 1.01     0.98<br>[-1,2-diphenylethylamide] |
| 6 | BOC—Phe—His—Sta—Leu—OCH₃<br>[tert-Butyloxycarbonyl-L-phenylalanyl-L-histidyl-(3S,4S)—statyl-L-leucine methyl ester] |
| 7 | BOC—Phe—His—Sta—Leu—NH—CH(CH₂C₆H₅)C₆H₅ (+)<br>     1.00 1.00    1.00<br>[-L-leucyl-(+)-1,2-diphenylethylamide] |
| 8 | BOC—Phe—His—Sta—Leu—NH—CH(CH₂C₆H₅)C₆H₅ (−)<br>     1.00 1.00    1.00<br>[-(−)-1,2-diphenylethylamide] |
| 9 | BOC—Phe—His—Sta—Leu—NH—CH₂—C₆H₅<br>     1.00 1.10    1.00<br>[-benzylamide] |
| 10 | BOC—Phe—His—Sta—Leu—NH—CH(CH₃)C₆H₅ (+)<br>     1.03 0.98    0.99<br>[-(+)-α-phenylethylamide] |
| 11 | BOC—Phe—His—Sta—Leu—NH—CH(CH₃)C₆H₅ (−)<br>     1.00 1.00    1.00<br>[-(−)-α-phenylethylamide] |
| 12 | BOC—Phe—His—Sta—Leu—NH—CH(CH₃)(1-naphthyl) (+)<br>     1.01 0.98    1.02<br>[-(+)-α-naphthylethylamide] |
| 13 | BOC—Phe—His—Sta—Leu—NH—CH(CH₃)(1-naphthyl) (−)<br>     1.02 0.97    1.00<br>[-(−)-α-naphthylethylamide] |
| 14 | BOC—Phe—His—Sta—Leu—NH—CH₂—C₆H₄—Cl (p)<br>     1.00 0.99    1.01<br>[-p-chlorobenzylamide] |
| 15 | BOC—Phe—His—Sta—Leu—NH—CH₂—C₆H₄—OCH₃ (p)<br>     0.99 1.00    1.01<br>[-p-methoxybenzylamide] |
| 16 | BOC—Phe—His—Sta—Leu—NH—(10,11-dihydro-5H-dibenzo[a,d]cycloheptenyl)=CH₂<br>     1.00 1.00    1.00<br>[-10,11-dihydro-5H—dibenzo[a,d]-cycloheptene amide] |
| 17 | BOC—Phe—His—Sta—Leu—NH—CH(CH₃)CH(OH)C₆H₅<br>     1.01 1.01    0.99<br>[-norpseudoephedrylamide] |

| Exm. No. | Peptide |
|---|---|
| 18 | BOC—Phe—His—Sta—Leu—NH-CH(Ph)-CH(OH)-Ph<br>        0.99  1.00     1.01<br>[-D,L-erythro-1,2-diphenyl-2-hydroxyethylamide] |
| 19 | BOC—Phe—His—Sta—Leu—NH-CH(Ph)-CH(OH)-Ph<br>        1.00  0.99     1.02<br>[-D,L-threo-1,2-diphenyl-2-hydroxyethylamide] |
| 20 | BOC—Phe—His—Sta—Leu—NH—CH₂—(2-pyridyl)<br>[-2-amidomethylpyridine] |
| 21 | BOC—Phe—His—Sta—Leu—NH—CH₂—(4-pyridyl)<br>[-4-amidomethylpyridine] |
| 22 | BOC—Phe—His—Sta—Leu—NH—(piperidyl)-N—CH₂—Ph<br>        1.02  1.00     0.98<br>[-4-amido-1-benzylpiperidine] |
| 23 | BOC—Phe—His—Sta—Leu—NH—(CH₂)₃—N—(CH₂CH₂OH)₂<br>        1.02  1.01     0.98<br>[-N—(3-amidopropyl)-diethanolamine] |
| 24 | Acetyl—Phe—His—AHPPA—Leu—NH—CH₂—Ph<br>        1.01  1.00            0.99 |
| 25 | BOC—Phe—His—AHPPA—Leu—NH—CH₂—Ph<br>        1.00  0.99            1.01 |
| 26 | BOC—Phe—His—Sta—Leu—Sta<br>        0.99  1.00     1.01 |

For the peptides prepared above, various analytical methods were carried out to verify the structure of the peptide products. The following table indicates which methods were employed and summarizes the results where practicable.

| Example No. | TLC[1] (No. of systems) | HPLC[2] | AA[3] | NMR[4] |
|---|---|---|---|---|
| 2  | 97% (2) | 97.1% | X | X |
| 3  | 97% (2) | 92.7% | X | X |
| 4  | 97% (2) | 93.8% | X | X |
| 5  | 98% (4) | 99%   | X | — |
| 6  | 98% (2) | 99%   |   | X |
| 7  | 98% (1) | 94.0% | X | X |
| 8  | 98% (1) | 99%   | X | X |
| 9  | 98% (1) | 97.8% | X | X |
| 10 | 98% (1) | 99.5% | X | X |
| 11 | 98% (1) | 99%   | X | X |
| 12 | 98% (1) | 93%   | X | X |
| 13 | 98% (1) | 85%   | X | X |
| 14 | 98% (1) | 95.5% | X | X |
| 15 | 98% (1) | 98.9% | X | X |
| 16 | 98% (1) | 96.7% | — | X |
| 17 | 98% (1) | 98.7% | X | X |
| 18 | 98% (1) | 98.5% | X | X |
| 19 | 98% (1) | 91%   | X | X |
| 20 | 98% (1) | —%    | — | X |
| 21 | 98% (1) | —     | — | X |
| 22 | 98% (1) | 90.7% | X | X |
| 23 | 98% (1) | 98.3% | X | X |
| 24 | 95% (1) | 92.1% | — | X |
| 25 | 95% (1) | 95.9% | X | X |
| 26 | 95% (1) | 95.0% | — | X |

[1]TLC = thin layer chromatography on silica gel; visualization by reagents which tend to detect peptides; no. of systems refers to number of different sovlent mixtures used to elute chromatograms; % refers to estimated purity.
[2]HPLC = high pressure liquid chromatography; detection be ultraviolet absorption at 240 nm or 210 nm; chromatography is reverse phase, values should by 1.00 ± 0.03.
[3]AA = amino acid analysis; peptides are hydrolyzed to their component amino acids, which are then quantitatively measured; values should be 1.00 ± 0.03.
[4]NMR = nuclear magnetic resonance spectroscopy at 300 MHz or 360 MHz for protons; X = spectrum consistent with structure; — = not performed.

EXAMPLE 27

Hog Renin Inhibition

An assay was carried out in order to determine the inhibitory potency of the peptides of the present invention. The assay measured the inhibition of hog kidney renin, and was in accordance with the procedure described in Rich et al., *J. Med. Chem.* 23:27, 1980, except that a pH of 7.3 was used. The results of the assay, illustrated in the table below, are expressed as $I_{50}$ values, which refers to the concentration of peptide inhibitor necessary to produce 50% inhibition of renin activity. This $I_{50}$ value is obtained typically by plotting data from four inhibitor concentrations. Pepstatin was used as an active control.

| Peptide | $I_{50}$ (M) |
|---|---|
| IBU[1]—His—Pro—Phe—His—Sta—Leu—benzylamide; | $1.3 \times 10^{-8}$ |
| IBU—His—Pro—Phe—His—Sta—Leu—2-phenylethylamide; | $3.0 \times 10^{-8}$ |
| IBU—His—Pro—Phe—His—Sta—Leu—3-phenylpropylamide; | $1.9 \times 10^{-8}$ |
| IBU—His—Pro—Phe—His—Sta—Leu—1,2-diphenylethylamide; | $5.6 \times 10^{-9}$ |
| BOC[2]—Phe—His—Sta—Leu—(+)[3]-1,2-diphenylethylamide; | $6.7 \times 10^{-9}$ |
| BOC—Phe—His—Sta—Leu—(−)-1,2-diphenylethylamide; | $2.3 \times 10^{-8}$ |

-continued

| Peptide | $I_{50}$ (M) |
|---|---|
| BOC—Phe—His—Sta—Leu—benzylamide; | $1.1 \times 10^{-8}$ |
| BOC—Phe—His—Sta—Leu—(+)-α-phenylethylamide; | $1.4 \times 10^{-8}$ |
| BOC—Phe—His—Sta—Leu—(−)-α-phenylethylamide; | $2.2 \times 10^{-8}$ |
| BOC—Phe—His—Sta—Leu—(+)-α-naphthylethylamide; | $1.1 \times 10^{-8}$ |
| BOC—Phe—His—Sta—Leu—(−)-α-naphthylethylamide; | $1.4 \times 10^{-8}$ |
| BOC—Phe—His—Sta—Leu—p-chlorobenzylamide; | $5.0 \times 10^{-9}$ |
| BOC—Phe—His—Sta—Leu—p-methoxybenzylamide; | $6.7 \times 10^{-9}$ |
| BOC—Phe—His—Sta—Leu—10,11-dihydro-5H—dibenzo[a,d]-cyclohepteneamide; | $5.8 \times 10^{-9}$ |
| BOC—Phe—His—Sta—Leu—D,L-threo-1,2-diphenyl-2-hydroxyethylamide; | $2.4 \times 10^{-8}$ |
| Acetyl—Phe—His—AHPPA—Leu—benzylamide; | $3.4 \times 10^{-9}$ |
| BOC—Phe—His—AHPPA—Leu—benzylamide; | $1.4 \times 10^{-9}$ |
| BOC—Phe—His—Sta—Leu—Sta. | $3.6 \times 10^{-8}$ |

[1] IBU = Iso-butyryl.
[2] BOC = Tert-butyloxycarbonyl.
[3] (+) refers to the optical rotation of the amine.

EXAMPLE 28

Human Renin Inhibition

An assay was carried out in order to determine the inhibitory potency of the peptides of the present invention. The assay measured the inhibition of human kidney renin purified as described in Bangham, D. R., Robertson, I., Robinson, J. I. S., Robinson, C. J., and Tree, M., *Clinical Science and Molecular Medicine*, 48 (Supp. 2): 136s–159s (1975), and further purified by affinity chromatography on pepstatin-aminohexyl-Sepharase as described in Poe, M., Wu, J. K., Florance, J. R., Radkey, J. A., Bennett, C. D., and Hoagsteen, K., *J. Biol. Chem.* (1982, in press). The assay was also in accordance with Poe et al. cited above. Results are expressed as $K_I$ values, which refer to the dissociation constant of the inhibited enzyme-inhibitor complex. This $K_I$ value was obtained as described above. Pepstatin was used as an active control. The results are set out in the table below.

| Peptide | $K_I$ (M) |
|---|---|
| IBU—His—Pro—Phe—His—Sta—Leu—benzylamide; | $1.2 \times 10^{-8}$ |
| BOC—Phe—His—Sta—Leu—(+)-1,2-diphenylethylamide; | $2.9 \times 10^{-8}$ |
| BOC—Phe—His—Sta—Leu—benzylamide; | $1.8 \times 10^{-8}$ |
| BOC—Phe—His—Sta—Leu—(2-amidomethylpyridine); | $2.5 \times 10^{-9}$ |
| BOC—Phe—His—Sta—Leu—(4-amido-1-benzyl-piperidine); | $6 \times 10^{-11}$ |
| BOC—Phe—His—Sta—Leu—[N—(3-amidopropyl)diethanolamine]; | $5.2 \times 10^{-8}$ |

What is claimed is:
1. A peptide of the formula:

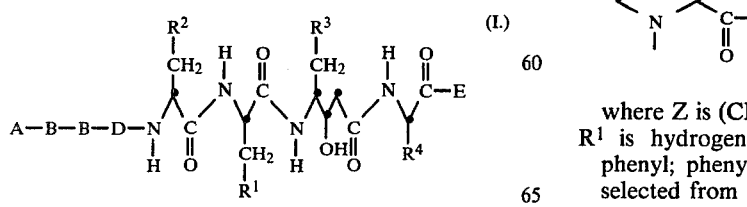

wherein:
A is hydrogen;

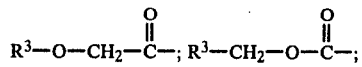

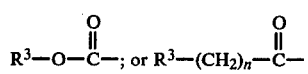

where n is 0 to 5 and $R^3$ has the same meaning as set out further below, and may additionally be hydrogen;

B is absent; glycyl; sarcosyl; or

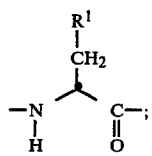

D is absent; or

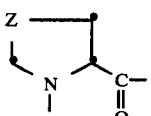

where Z is $(CH_2)_n$ and n is 1 or 2; or —S—;

$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

$R^3$ is $C_{3-6}$ alkyl; $C_{3-7}$ cycloalkyl; phenyl; or $C_{3-7}$ cycloalkyl or phenyl mono-substituted with a member selected from the group consisting of methyl, trifluoromethyl, hydroxy, methoxy, fluoro, chloro, bromo, and iodo;

$R^4$ is hydrogen; or

where $R^5$ is hydrogen; $C_{1-4}$ alkyl; hydroxy; or $C_{3-7}$ cycloalkyl; and

E is $$-Y-(CH_2)_n-R^6 \qquad (1)$$

where
Y is —NH— or —O—;
n is 0 to 5; and
$R^6$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di- $C_{1-4}$ alkylamino, and halo; amino; mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino;

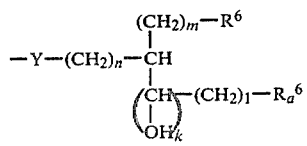

where
Y is as defined above;
n is 0 or 1;
k is 0 or 1;
l is 1 to 4;
m is 1 to 4; and
$R^6$ and $R_a^6$ may be the same or different and have the same meaning as $R^6$ above and $R_a^6$ may additionally be

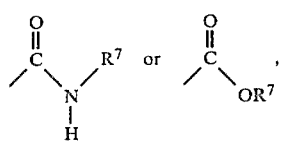

where $R^7$ is hydrogen or $C_{1-3}$alkyl; or

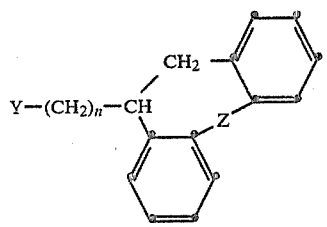

where
Y is as defined above;
n is 0 or 1; and
Z is (a) 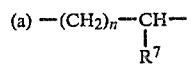

where
n is 0 or 1; and
$R^7$ is as defined above; or (b) 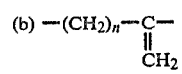

where
n is 0 or 1;
wherein all of the asymmetric carbon atoms have an S configuration, except for those in the B, D, and E substituents, which may have an S or R configuration; and a pharmaceutically acceptable salt thereof.

2. A peptide according to claim 1 wherein the peptide is a member selected from the group consisting essentially of:
IBU—His-Pro-Phe-His-Sta-Leu-benzylamide;
IBU—His-Pro-Phe-His-Sta-Leu-2-phenylethylamide;
IBU—His-Pro-Phe-His-Sta-Leu-3-phenylpropylamide;
IBU—His-Pro-Phe-His-Sta-Leu-1,2-diphenylethylamide;
BOC—Phe-His-Sta-Leu-(+)-1,2-diphenylethylamide;
BOC—Phe-His-Sta-Leu-(−)-1,2-diphenylethylamide;
BOC—Phe-His-Sta-Leu-benzylamide;
BOC—Phe-His-Sta-Leu-(+)-α-phenylethylamide;
BOC—Phe-His-Sta-Leu-(−)-α-phenylethylamide;
BOC—Phe-His-Sta-Leu-(+)-α-naphthylethylamide;
BOC—Phe-His-Sta-Leu-(−)-α-naphthylethylamide;
BOC—Phe-His-Sta-Leu-p-chlorobenzylamide;
BOC—Phe-His-Sta-Leu-p-methoxybenzylamide;
BOC—Phe-His-Sta-Leu-10,11-dihydro-5H-dibenzo[a,d]-cycloheteneamide;
BOC—Phe-His-Sta-Leu-D,L-threo-1,2-diphenyl-2-hydroxyethylamide;
BOC—Phe-His-Sta-Leu-Sta;
BOC—Phe-His-AHPPA-Leu-benzylamide;
Acetyl—Phe-His-AHPPA-Leu-benzylamide;
BOC—Phe-His-Sta-Leu-(2-amidomethylpyridine);
BOC—Phe-His-Sta-Leu-(4-amidomethylpyridine);
BOC—Phe-His-Sta-Leu-(4-amido-1-benzylpiperidine);

BOC—Phe-His-Sta-Leu-[N-(3-amidopropyl)diethanolamine];
BOC—Phe-His-AHPPA-Leu-(2-amidomethylpyridine);
BOC—Phe-His-ACHPA-Ile-(2-amidomethylpyridine);
IVA-His-D-Pro-Phe-His-ACHPA-Ile-(2-amidomethylpyridine).

3. A pharmaceutical composition for treating renin-associated hypertension or hyperoldosteronism, comprising a pharmaceutical carrier and a therapeutically effective amount of a peptide of the formula:

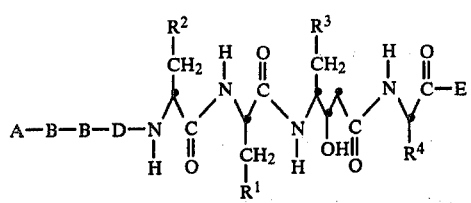 (I.)

wherein:
A is hydrogen;

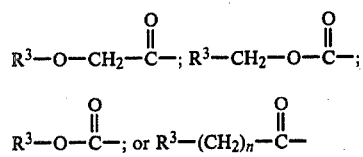

where n is 0 to 5 and $R^3$ has the same meaning as set out further below, and may additionally be hydrogen;
B is absent; glycyl; sarcosyl; or

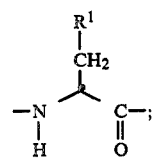

D is absent; or

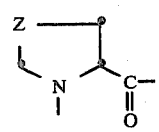

where Z is $(CH_2)_n$ and n is 1 or 2; or —S—;
$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;
$R^2$ is hydrogen $C_{1-4}$; alkyl, phenyl; phenyl mono-substituted with a member selected from the group consisting of methyl, trifluoromethyl, hydroxy, methoxy, fluoro, chloro, bromo, and iodo; or indolyl;
$R^3$ is $C_{3-6}$ alkyl; $C_{3-7}$ cycloalkyl; phenyl; or $C_{3-7}$cycloalkyl or phenyl mono-substituted with a member selected from the group consisting of methyl, trifluoromethyl, hydroxy, methoxy, fluoro, chloro, bromo, and iodo;
$R^4$ is hydrogen; or

where $R^5$ is hydrogen; $C_{1-4}$ alkyl; hydroxy; or $C_{3-7}$ cycloalkyl; and
E is

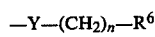 (1)

where
Y is —NH— or —O—;
n is 0 to 5; and
$R^6$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di-$C_{1-4}$alkylamino, and halo; amino; mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino;

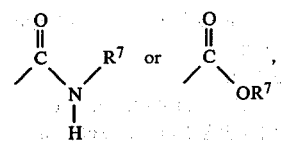 (2)

where
Y is as defined above;
n is 0 or 1;
k is 0 or 1;
l is 1 to 4;
m is 1 to 4; and
$R^6$ and $R_a^6$ may be the same or different and have the same meaning as $R^6$ above and $R_a^6$ may additionally be

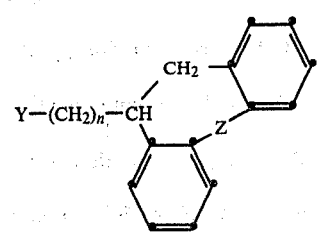

where $R^7$ is hydrogen or $C_{1-3}$alkyl; or (3)

where
Y is as defined above;
n is 0 or 1; and

Z is (a) 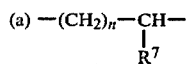

where
n is 0 or 1; and
R⁷ is as defined above; or (b) 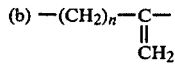

where
n is 0 or 1;
wherein all of the asymmetric carbon atoms have an S configuration, except for those in the B, D, and E substituents, which may have an S or R configuration; and a pharmaceutically acceptable salt thereof.

4. A composition according to claim 3 wherein the peptide is a member selected from the group consisting essentially of:
IBU—His-Pro-Phe-His-Sta-Leu-benzylamide;
IBU—His-Pro-Phe-His-Sta-Leu-2-phenylethylamide;
IBU—His-Pro-Phe-His-Sta-Leu-3-phenylpropylamide;
IBU—His-Pro-Phe-His-Sta-Leu-1,2-diphenylethylamide;
BOC—Phe-His-Sta-Leu-(+)-1,2-diphenylethylamide;
BOC—Phe-His-Sta-Leu-(−)-1,2-diphenylethylamide;
BOC—Phe-His-Sta-Leu-benzylamide;
BOC—Phe-His-Sta-Leu-(+)-α-phenylethylamide;
BOC—Phe-His-Sta-Leu-(−)-α-phenylethylamide;
BOC—Phe-His-Sta-Leu-(+)-α-naphthylethylamide;
BOC—Phe-His-Sta-Leu-(−)-α-naphthylethylamide;
BOC—Phe-His-Sta-Leu-p-chlorobenzylamide;
BOC—Phe-His-Sta-Leu-p-methoxybenzylamide;
BOC—Phe-His-Sta-Leu-10,11-dihydro-5H-dibenzo[a,d]-cycloheptenamide;
BOC—Phe-His-Sta-Leu-D,L-threo-1,2-diphenyl-2-hydroxyethylamide;
BOC—Phe-His-Sta-Leu-Sta;
BOC—Phe-His-AHPPA-Leu-benzylamide;
Acetyl—Phe-His-AHPPA-Leu-benzylamide;
BOC—Phe-His-Sta-Leu-(2-amidomethylpyridine);
BOC—Phe-His-Sta-Leu-(4-amidomethylpyridine);
BOC—Phe-His-Sta-Leu-(4-amido-1-benzylpiperidine);
BOC—Phe-His-Sta-Leu-[N-(3-amidopropyl)diethanolamine];
BOC—Phe-His-AHPPA-Leu-(2-amidomethylpyridine);
BOC—Phe-His-ACHPA-Ile-(2-amidomethylpyridine);
IVA-His-D-Pro-Phe-His-ACHPA-Ile-(2-amidomethylpyridine).

5. A method of treating renin-associated hypertension comprising administering to a patient in need of such treatment, a therapeutically effective amount of a peptide of the formula:

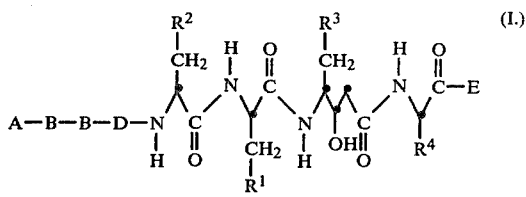

wherein:
A is hydrogen;

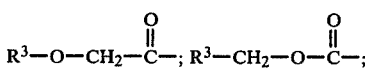

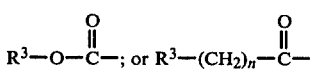

where n is 0 to 5 and R³ has the same meaning as set out further below, and may additionally be hydrogen;
B is absent; glycyl; sarcosyl; or

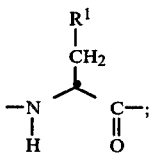

D is absent; or

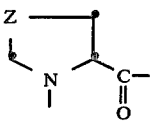

where Z is $(CH_2)_n$ and n is 1 or 2; or —S—;
R¹ is hydrogen; $C_{1-4}$alkyl; hydroxy $C_{1-4}$alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$alkyl; guanidyl $C_{2-3}$alkyl; or methylthiomethyl;
R² is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;
R³ is $C_{3-6}$alkyl; $C_{3-7}$cycloalkyl; phenyl; or $C_{3-7}$cycloalkyl or phenyl mono-substituted with a member selected from the group consisting of methyl, trifluoromethyl, hydroxy, methoxy, fluoro, chloro, bromo, and iodo;
R⁴ is hydrogen; or

where R⁵ is hydrogen; $C_{1-4}$ alkyl; hydroxy; or $C_{3-7}$ cycloalkyl; and
E is —Y—$(CH_2)_n$—R⁶     (1)

where
- Y is —NH— or —O—;
- n is 0 to 5; and
- $R^6$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di-$C_{1-4}$alkylamino, and halo; amino; mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino;

$$-Y-(CH_2)_n-\underset{\underset{OH_k}{|}}{\overset{\overset{(CH_2)_m-R^6}{|}}{CH}}-CH-(CH_2)_l-R_a^6 \quad (2)$$

where
- Y is as defined above;
- n is 0 or 1;
- k is 0 or 1;
- l is 1 to 4;
- m is 1 to 4; and
- $R^6$ and $R_a^6$ may be the same or different and have the same meaning as $R^6$ above and $R_a^6$ may additionally be $$\overset{O}{\underset{H}{\overset{\|}{C}}}\underset{N}{\diagdown}R^7 \quad \text{or} \quad \overset{O}{\underset{}{\overset{\|}{C}}}\diagdown OR^7,$$

where $R^7$ is hydrogen or $C_{1-3}$alkyl; or $$(3) \quad Y-(CH_2)_n-CH\diagdown \overset{CH_2-\text{(phenyl)}}{\underset{Z-\text{(phenyl)}}{}}$$

where
- Y is as defined above;
- n is 0 or 1; and
- Z is (a) $-(CH_2)_n-\underset{\underset{R^7}{|}}{CH}-$ where
- n is 0 or 1; and
- $R^7$ is as defined above; or (b) $-(CH_2)_n-\underset{\underset{CH_2}{\|}}{C}-$ where
n is 0 or 1;
wherein all of the asymmetric carbon atoms have an S configuration, except for those in the B, D, and E substituents, which may have an S or R configuration; and a pharmaceutically acceptable salt thereof.

6. A method according to claim 5 wherein the peptide is a member selected from the group consisting essentially of:

IBU—His-Pro-Phe-His-Sta-Leu-benzylamide;
IBU—His-Pro-Phe-His-Sta-Leu-2-phenylethylamide;
IBU—His-Pro-Phe-His-Sta-Leu-3-phenylpropylamide;
IBU—His-Pro-Phe-His-Sta-Leu-1,2-diphenylethylamide;
BOC—Phe-His-Sta-Leu-(+)-1,2-diphenylethylamide;
BOC—Phe-His-Sta-Leu-(−)-1,2-diphenylethylamide;
BOC—Phe-His-Sta-Leu-benzylamide;
BOC—Phe-His-Sta-Leu-(+)-α-phenylethylamide;
BOC—Phe-His-Sta-Leu-(−)-α-phenylethylamide;
BOC—Phe-His-Sta-Leu-(+)-α-naphthylethylamide;
BOC—Phe-His-Sta-Leu-(−)-α-naphthylethylamide;
BOC—Phe-His-Sta-Leu-p-chlorobenzylamide;
BOC—Phe-His-Sta-Leu-p-methoxybenzylamide;
BOC—Phe-His-Sta-Leu-10,11-dihydro-5H-dibenzo[a,d]-cyclohepteneamide;
BOC—Phe-His-Sta-Leu-D,L-threo-1,2-diphenyl-2-hydroxyethylamide;
BOC—Phe-His-Sta-Leu-Sta;
BOC—Phe-His-AHPPA-Leu-benzylamide;
Acetyl—Phe-His-AHPPA-Leu-benzylamide;
BOC—Phe-His-Sta-Leu-(2-amidomethylpyridine);
BOC—Phe-His-Sta-Leu-(4-amidomethylpyridine);
BOC—Phe-His-Sta-Leu-(4-amido-1-benzylpiperidine);
BOC—Phe-His-Sta-Leu-[N-(3-amidopropyl)diethanolamine];
BOC—Phe-His-AHPPA-Leu-(2-amidomethylpyridine);
BOC—Phe-His-ACHPA-Ile-(2-amidomethylpyridine);
IVA-His-D-Pro-Phe-His-ACHPA-Ile-(2-amidomethylpyridine).

7. A method of treating renin-associated hyperaldosteronism, comprising administering to a patient in need of such treatment, a therapeutically effective amount of a peptide of the formula:

$$A-B-B-D-\underset{\underset{H}{|}}{N}-\underset{\underset{O}{\|}}{C}\diagup \overset{\overset{R^2}{|}}{\underset{\underset{CH_2}{|}}{CH_2}}\diagdown \underset{\underset{H}{|}}{N}-\underset{\underset{OH}{|}}{C}-\underset{\underset{R^1}{|}}{CH_2}\diagdown \underset{\underset{H}{|}}{N}-\underset{\underset{O}{\|}}{C}-E \quad (I.)$$

wherein:
A is hydrogen;

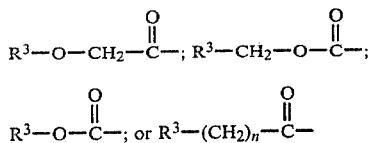

where n is 0 to 5 and R³ has the same meaning as set out further below, and may additionally be hydrogen;

B is absent; glycyl; sarcosyl; or

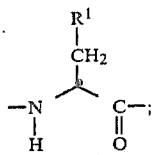

D is absent; or

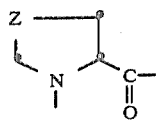

where Z is $(CH_2)_n$ and n is 1 or 2; or —S—;

R¹ is hydrogen; $C_{1-4}$alkyl; hydroxy $C_{1-4}$alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$alkyl; guanidyl $C_{2-3}$alkyl; or methylthiomethyl;

R² is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

R³ is $C_{3-6}$alkyl; $C_{3-7}$cycloalkyl; phenyl; or $C_{3-7}$cycloalkyl or phenyl mono-substituted with a member selected from the group consisting of methyl, trifluoromethyl, hydroxy, methoxy, fluoro, chloro, bromo, and iodo;

R⁴ is hydrogen; or

where R⁵ is hydrogen; $C_{1-4}$alkyl; hydroxy; or $C_{3-7}$cycloalkyl; and

E is

   (1)

where
Y is —NH— or —O—;
n is 0 to 5; and
R⁶ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di-$C_{1-4}$alkylamino, and halo; amino; mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and $C_{1-4}$alkylamino;

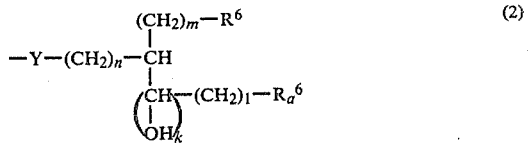   (2)

where
Y is as defined above;
n is 0 or 1;
k is 0 or 1;
l is 1 to 4;
m is 1 to 4; and
R⁶ and $R_a^6$ may be the same or different and have the same meaning as R⁶ above and $R_a^6$ may additionally be

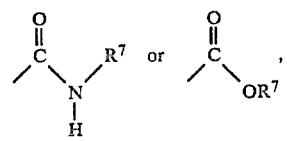

where R⁷ is hydrogen or $C_{1-3}$alkyl; or

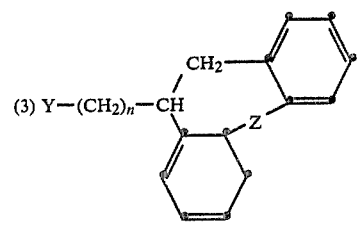

where
Y is as defined above;
n is 0 or 1; and
Z is

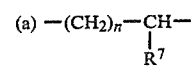   (a)

where
n is 0 or 1; and
R⁷ is as defined above; or

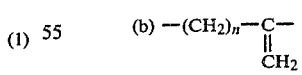   (b)

where
n is 0 or 1;
wherein all of the asymmetric carbon atoms have an S configuration, except for those in the B, D, and E substituents, which may have an S or R configuration; and a pharmaceutically acceptable salt thereof.

8. A method of determining the presence of renin-associated hypertension in a patient, comprising administering to such a patient, at a hypotensive dosage level and as a single dose, a peptide of the formula:

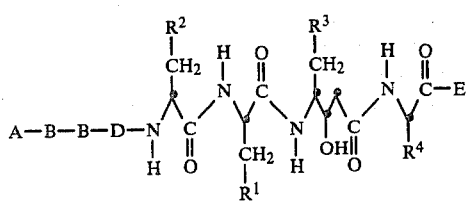 (I.)

wherein:
A is hydrogen;

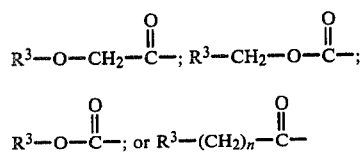

where n is 0 to 5 and $R^3$ has the same meaning as set out further below, and may additionally be hydrogen;
B is absent; glycyl; sarcosyl; or

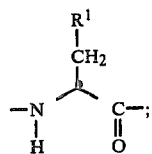

D is absent; or

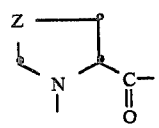

where Z is $(CH_2)_n$ and n is 1 or 2; or —S—;
$R^1$ is hydrogen; $C_{1-4}$alkyl; hydroxy $C_{1-4}$alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$alkyl; guanidyl $C_{2-3}$alkyl; or methylthiomethyl;
$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;
$R^3$ is $C_{3-6}$alkyl; $C_{3-7}$cycloalkyl; phenyl; or $C_{3-7}$cycloalkyl or phenyl mono-substituted with a member selected from the group consisting of methyl, trifluoromethyl, hydroxy, methoxy, fluoro, chloro, bromo, and iodo;
$R^4$ is hydrogen; or

where $R^5$ is hydrogen; $C_{1-4}$alkyl; hydroxy; or $C_{3-7}$cycloalkyl; and
E is

 (1)

where
Y is —NH— or —O—;
n is 0 to 5; and
$R^6$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di-$C_{1-4}$alkylamino, and halo; amino; mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino;

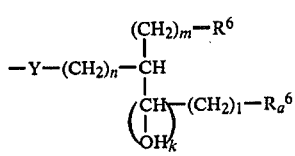 (2)

where
Y is as defined above;
n is 0 or 1;
k is 0 or 1;
l is 1 to 4;
m is 1 to 4; and
$R^6$ and $R_a^6$ may be the same or different and have the same meaning as $R^6$ above and $R_a^6$ may additionally be

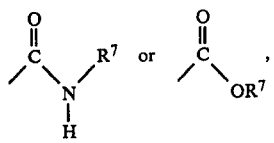

where $R^7$ is hydrogen or $C_{1-3}$alkyl; or

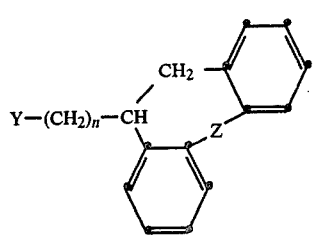 (3)

where
Y is as defined above;
n is 0 or 1; and
Z is (a) 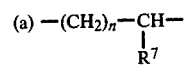

where
n is 0 or 1; and
$R^7$ is as defined above; or (b) 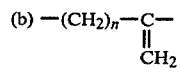
where
n is 0 or 1;
wherein all of the asymmetric carbon atoms have an S configuration, except for those in the B, D, and E substituents, which may have an S or R configuration; and a pharmaceutically acceptable salt thereof; followed by monitoring of said patient's blood pressure.
* * * * *